(12) United States Patent
Li (10) Patent No.: US 11,324,844 B2
(45) Date of Patent: May 10, 2022

(54) UV STERILIZATION DEVICE FOR BOARD-TYPE KITCHENWARE

(71) Applicant: Xiaohui Li, Shenzhen (CN)

(72) Inventor: Xiaohui Li, Shenzhen (CN)

( * ) Notice: Subject to any disclaimer, the term of this patent is extended or adjusted under 35 U.S.C. 154(b) by 392 days.

(21) Appl. No.: 16/538,786

(22) Filed: Aug. 12, 2019

(65) Prior Publication Data

US 2020/0289684 A1 Sep. 17, 2020

(30) Foreign Application Priority Data

Mar. 14, 2019 (CN) .......................... 201910194265.2

(51) Int. Cl.
*A61L 2/10* (2006.01)
*A61L 2/26* (2006.01)

(52) U.S. Cl.
CPC .. *A61L 2/10* (2013.01); *A61L 2/26* (2013.01)

(58) Field of Classification Search
CPC ..................................... A61L 2/10; A61L 2/26
See application file for complete search history.

(56) References Cited

U.S. PATENT DOCUMENTS

| 5,010,365 | A * | 4/1991 | Hatanaka | ............. | G03G 15/757 |
| | | | | | 399/111 |
| 7,560,706 | B1 * | 7/2009 | Castelluccio | ............. | A61L 2/10 |
| | | | | | 250/365 |
| 2010/0266445 | A1 * | 10/2010 | Campagna | ............. | A61L 2/24 |
| | | | | | 422/23 |
| 2017/0224858 | A1 * | 8/2017 | Stibich | ............. | A61L 2/26 |

FOREIGN PATENT DOCUMENTS

| CN | 107261174 A | * | 10/2017 | | |
| CN | 107930286 A | * | 4/2018 | | |
| JP | 3037304 B2 | * | 4/2000 | ............. | A47L 9/1472 |

(Continued)

OTHER PUBLICATIONS

Hepner Racing Products 2006 Catalog, 2006, Hepner Racing, p. 83, https://images.toolsid.com/hrp/items/pdf/hrp-product-catalog.pdf (Accessed Oct. 20, 2021) (Year: 2006).*

(Continued)

*Primary Examiner* — Kevin Joyner
*Assistant Examiner* — Changru Chen (57) ABSTRACT

A UV sterilization device for a board-type kitchenware includes a base with a driving member being received therein and defining a first motor, a left work-board, a right work-board, with a receiving room being formed between the left and right work-boards for receiving the board-type kitchenware therein, and a UV sterilization module connected to the first motor, longitudinally arranged on the inside of the left and right work-boards and horizontally sliding relative to the left and right work-boards. The first motor is configured to drive the UV sterilization module to slide so as to sterilize the board-type kitchenware received in the receiving room. The present structure not only can have a good disinfection and bactericidal effect on the harmful bacteria, pathogenic bacteria and molds left on the kitchenware with a minimize disinfection time, but also can reciprocate sterilization of the board-type kitchenware to achieve all-round sterilization by simple operation.

19 Claims, 11 Drawing Sheets

(56) References Cited

FOREIGN PATENT DOCUMENTS

| JP | 4079734 B2 | * | 4/2008 | |
|----|------------|---|--------|---|
| KR | 20110014781 A | * | 2/2011 | |
| KR | 200480835 Y1 | * | 7/2016 | |
| KR | 20180058884 A | * | 6/2018 | |
| WO | WO-2011027135 A2 | * | 3/2011 | ............. C01B 13/11 |

OTHER PUBLICATIONS

Firgelli Automations, Linear Bearings 101—What is a Linear Slide Bearing and how do they work., Sep. 16, 2011, https://www.youtube.com/watch?v=-UqygYJvPXU (Accessed Oct. 20, 2021) (Year: 2011).*
Technic, Axle Connector 2×3 with Ball Joint Socket, Open Lower Axle Holes, 2009, Lego (Year: 2009).*
Technic Ball Joint 2×7 with 2 Ball Joint, 1999, Lego (Year: 1999).*
Snapfit principe reversibilite, Apr. 16, 2008, Wikipedia, https://commons.wikimedia.org/wiki/File:Snapfit_principe_reversibilite.svg (Accessed Oct. 20, 2021) (Year: 2008).*
8297 Technic Instruction Manual, 2008, Lego, https://www.lego.com/en-us/service/buildinginstructions/8297 (Year: 2008).*
Translation of CN_107261174_A_I (Year: 2017).*
Translation of CN_107930286_A_I (Year: 2018).*
Translation of JP_3037304_B2_I (Year: 2000).*
Translation of JP_4079734_B2_I (Year: 2008).*
Translation of KR_200480835_Y1_I (Year: 2004).*
Translation of KR_20110014781_A_I (Year: 2011).*
Translation of KR_20180058884_A_I (Year: 2018).*

* cited by examiner

UV STERILIZATION DEVICE FOR BOARD-TYPE KITCHENWARE

BACKGROUND

1. Technical Field

The present disclosure generally relates to tableware disinfection and sterilization devices field, and especially relates to a UV sterilization device for a board-type kitchenware.

2. Description of Related Art

As we all known, in order to ensure food sanitation, kitchenware is often needed disinfection before using it. In general, kitchenware is generally received in cupboards to disinfection. However, such disinfection way is very inconvenient for board-type kitchenware, such as cutting boards with a large size. For the board-type kitchenware with large size, a conventional disinfection method is that the cutting boards or plate cutters are usually disinfected by means of salt washing or drying. But, such disinfection method not only takes time and energy, but also has limited disinfection effect.

SUMMARY

The technical problems to be solved: in view of the shortcomings of the related art, the present disclosure relates to a UV sterilization device for a board-type kitchenware which can not only have a good disinfection and bactericidal effect on the harmful bacteria, pathogenic bacteria and molds left on the kitchenware with a minimize disinfection time, but also reciprocate sterilization for the board-type kitchenware to achieve all-round sterilization by simple operation.

The technical solution adopted for solving technical problems of the present disclosure is:

a UV sterilization device for a board-type kitchenware includes a base including a driving member received therein and the driving member including a first motor, a workboard including a left work-board and a right work-board, the left work-board and the right work-board structurally consistent with each other and symmetrically connected to front and rear sides of the base, and a receiving room formed between the left work-board and the right work-board for receiving the board-type kitchenware therein, and a UV sterilization module longitudinally arranged on the inside of the left and right work-boards and horizontally sliding relative to the left and right work-boards. The first motor is connected with the UV sterilization module and configured to drive the UV sterilization module to slide so as to sterilize the board-type kitchenware received in the receiving room.

Wherein the UV sterilization device further includes a rotating member and a transmission member, the rotating member including a rotating gear fixed with the first motor, and the transmission member including a pair of variable gears respectively arranged on both sides of the rotating gear and partially meshed with the rotating gear, a main shaft fixed with one of the pair of variable gears, and a pair of screw rods with a corresponding end thereof rotatably connected with two opposite portions of the main shaft; two opposite ends of the UV sterilization module slidably arranged on the pair of screw rods, respectively, the first motor configured to drive the rotating gear to rotate and make the variable gear, the main shaft and the pair of screw rods rotate so as to further drive the UV sterilization module to slide with the pair of screw rods.

Wherein the transmission member further includes a pair of end cones respectively fixed at the two opposite portions of the main shaft, the pair of screw rods each including a connecting gear formed on a portion adjacent to the main shaft, the end cone partially meshed with a corresponding connecting gear so as to rotatably connect the pair of screw rods and the main shaft.

Wherein the UV sterilization device further includes a sliding rail, and each of the left and right work-boards includes a lateral first receiving slot formed on their respective top inner side and bottom inner side for receiving the sliding rail therein.

Wherein each of the left and right work-boards includes a longitudinal second receiving slot on their respective both sides to connect with the first receiving slot, all the main shaft and the pair of end cones received in one of the second receiving slots, a front cover arranged on each of the left work-board and the right work-board and covered on the second receiving slot.

Wherein the first receiving slot includes a first U-shaped slot for fixing with the pair of screw rods, and the second receiving slot includes a second U-shaped slot for fixing with the main shaft.

Wherein the sliding rail includes a sliding groove and a sliding block sliding relative to the sliding groove, the sliding block including a sliding portion slidably arranged on the sliding groove, a thread, groove meshed with the screw rod and an inserting slot for inserting the UV sterilization module therein.

Wherein the sliding groove is a T-shaped configuration and the sliding portion is a T-shaped plate.

Wherein the left work-board and the right work-board respectively include a reflecting plate mounted between the front covers.

Wherein the UV sterilization module includes a surface plate, a heat dissipation shell fixed with the surface plate, and an end cap arranged on two ends of the surface plate and the heat dissipation shell and including a buckle inserted into the inserting slot for tightly fixing the UV sterilization module with the sliding block.

Wherein the base includes a main body, a base plate fixed with the bottom of the main body and a switching panel, the main body including a hooking portion and an installing groove formed on a lower side end of the main body, with the installing groove including a touching tablet and a touching PCB therein; each of the left and right work-boards including a snapping hole engaged with the hooking portion for tightly fixing the base with the left and right work-boards, and the switching panel covering on the installing groove.

Wherein the main body includes a receiving recess for receiving the rotating gear therein, and the variable gear includes a housing and a gear shaft, the housing fixed into the receiving recess via the gear shaft.

Wherein the main shaft includes a plurality of ribs protruding outward from the bottom thereof, and the inserting rod is connected with the upper of the gear shaft and includes an opening slot, the rib inserting into the opening slot for the main shaft with the variable gear.

Wherein the UV sterilization device further includes a pair of transmission boxes respectively arranged on two opposite sides of the base and axially connected with the base so that the board-type kitchenware positioned on the pair of transmission boxes can be fed into or discharged out of the receiving room.

Wherein the transmission box includes a transmitting body, a transmitting device received in the transmitting body and a power plant fixed on a sidewall of the transmitting body, and the power plant is configured to drive the transmitting device to rotate so that the board-type kitchenware positioned on the pair of transmission boxes can be fed into or discharged out of the receiving room.

Wherein the transmitting device includes an active roller and a passive roller, and the transmitting body includes a rim for accommodating the active roller and the passive roller thereon, the rim including a partition for separating the active roller from the passive roller.

Wherein the power plant includes a pair of first pulleys, a large-diameter pulley, a small-diameter pulley and a second motor, the active roller sleeved around one of the first pulleys, the other first pulley coaxially fixed with the large-diameter pulley, and the small-diameter pulley fixedly connected with the second motor.

Wherein the base includes a pedestal protruding outward from two opposite sides thereof, the pedestal including an installing hole, the transmitting body including a connecting recess attached to the inner wall of the pedestal and an installing shaft sleeved on the installing hole, and the transmission box can be rotated around the pedestal in a range of 0-90 degrees.

Wherein each of the left work-hoard and the right work-board includes a tableware hook formed on their respective upper portions thereof and bent to form two U-shaped structures thereon, each of the two U-shaped structures including a middle rod, a lateral rod connected to the middle rod and an end portion formed on a distal end of the lateral rod, the two middle rods close to each other and the two end portions bent towards each other.

Wherein the distance between the two middle rods and the upper portion of the left and right work-boards is greater than the distance between the two lateral rods and the upper portion of the left and right work-boards; while, the distance between the two end portions and the upper portion of the left and right work-boards is greater than the distance between the two lateral rods and the upper portion of the left and right work-boards.

The present disclosure provides the advantages as below.

The UV sterilization module of the present disclosure can not only have a good disinfection and bactericidal effect on the harmful bacteria, pathogenic bacteria and molds left on the kitchenware with a minimize disinfection time, but also reciprocate sterilization of the board-type kitchenware to achieve all-round sterilization by simply operating the UV sterilization module sliding relative to the left and right work-boards.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

The element labels according to the exemplary embodiment of the present disclosure shown as below:

UV sterilization device 100, board-type kitchenware base 10, opposite sides 10a, driving member 101, first motor 1011, main body 11, 11a lower side end, hooking portion 111, installing groove 112, touching tablet 113, touching PCB 114, receiving recess 115, base plate 12, switching panel 13, pedestal 14, installing hole 15, work-hoard 20, upper portion 20a, top inner side 20b, bottom inner side 20c, left work-board 21, right work-board receiving room 23, first receiving slot 24, first U-shaped slot 241, second receiving slot 25, second U-shaped slot 251, front cover 26, reflecting plate 27, snapping hole 28, UV sterilization module 30, opposite ends 30a, surface cover 31, heating dissipation shell 32, end cap 33, buckle 331, rotating member 40, rotating gear 41, transmission member 50, variable gear 51, housing 511, gear shaft 512, inserting rod 513, opening slot 5131, main shaft 52, opposite portions 52a, rib 521, screw rod 53, end 53a, end cone 54, connecting gear 55, sliding rail 60, sliding groove 61, sliding block 62, sliding portion 62, thread groove 622, inserting slot 623, transmission box 70, transmitting body 71, partition 711, connecting recess 712, installing shaft 713, rim 714, transmitting device 72, active roller 721, passive roller 722, power plant 73, first pulley 731, large-diameter pulley 732, small-diameter pulley 733, second motor 734, tableware hook 80, U-shaped structure 81, middle rod 810 lateral rod 811, end portion 8110.

DETAILED DESCRIPTION

The disclosure is illustrated by way of example and not by way of limitation in the figures of the accompanying drawings, in which like reference numerals indicate similar elements.

In the description of the present disclosure, it needs to be understood that the terms mentioned below: "central", "longitudinal", "transverse", "length", "width", "thickness", "upper", "below", "front", "back", "left", "right", "vertical", "horizontal", "top", "bottom", "inner", "outer", "clockwise", "anticlockwise", etc, are shown in the specification of the present disclosure. The indicated orientation or position of the terms shown in the detailed description is based on the orientation or position shown in the figures of the accompanying drawings of the present disclosure, which is only to easily simplify the description of the present disclosure, but not indicated that the devices or elements of the present disclosure should have a particular orientation or should be designed and operated in a particular orientation. So the terms illustrated in the detail description are not by way of the limitation of the present disclosure.

In addition, the terms such as "first" and "second" shown in the specification are only used to describe, but not indicated that the elements of the present disclosure is important or represented the amount of the elements. That the features limited by the terms of "first" and "second" may explicitly or implicitly include one or more features. In the description of the present disclosure, the meaning of the term "a plurality of" is not less than two unless it is specifically illustrated.

In the present disclosure, except where specifically otherwise illustrated or limited, the terms "install", "connect", "link" and "fix" used herein should be understood in a broad sense. Such as, the meaning may be tight connection, removable connection or integrated connection. The meaning may also be mechanical connection, electrical connection, direct connection or indirect connection through intermediaries, or internal connection within two elements. The meaning of the terms used herein may be understood by one of ordinary skill in the related art according to specific conditions of the present disclosure.

Referring to FIGS. 1-18, a UV sterilization device 100 for a board-type kitchenware 200 in accordance with an exemplary embodiment is provided. The UV sterilization device 100 includes:

a base 10 which includes a driving member 101 received therein, and the driving member 101 includes a first motor 1011;

a work-board 20 which includes a left work-board 21 and a right work-board 22. The left work-board 21 and the right work-board 22 is structurally consistent with each other and symmetrically connected to the front and rear sides of the base 10, and a receiving room 23 formed between the left work-board 21 and the work-board 22 for receiving the board-type kitchenware 200 therein;

and a UV sterilization module 30 longitudinally arranged on the inside of the left and right work-boards 21, 22 and horizontally sliding relative to the left and right work-boards 21, 22;

The first motor 1011 is connected with the UV sterilization module 30 and configured to drive the UV sterilization module 30 to slide so as to sterilize the board-type kitchenware 200 received in the receiving room 23.

The UV sterilization module 30 of the present disclosure can have a good disinfection and bactericidal effect on the harmful bacteria, pathogenic bacteria and molds left on the kitchenware with a minimize disinfection time. Furthermore, the UV sterilization module 30 can horizontally slide relative to the left work-hoard 21 and the right work-board 22 for reciprocating sterilization of the board-type kitchenware 200 received in the receiving room 23, thereby achieving all-round sterilization by simple operation.

In an exemplary embodiment of the present disclosure, light emitted from the UV sterilization module 30 includes ultraviolet light at the wavelength of 200~290 nm UVC band and blue light at the wavelength of 400~460 nm. The ultraviolet light of UVC band is mainly played as the role of sterilization, thereby such ultraviolet light in this wavelength range has excellent killing effect on most bacteria and pathogenic bacteria found so far. Therefore, it has a good antibacterial and antitoxic effect on the harmful bacteria, pathogenic bacteria and molds left on the board-type kitchenware 200. In addition, the blue light is mainly played as the role of anti-mold so that it is usually used to remove molds, thereby an excellent disinfection and anti-mold effect by simple operation can be achieved.

In an exemplary embodiment of the present disclosure, the first motor 1011 is a stepping motor which can effectively control its rotating speed and forward and reverse rotation. In this way, it can achieve laterally reciprocating movement of the UV sterilization module 30 to further obtain all-round sterilization effect without dead angle.

Figure 1:
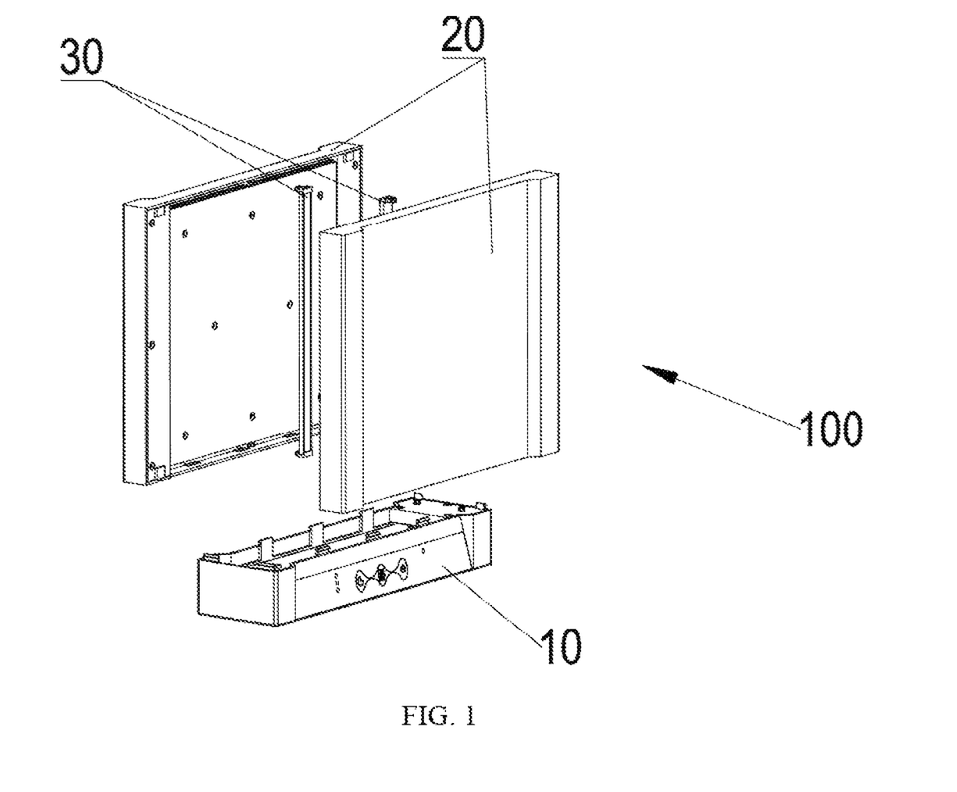
FIG. 1 is an exploded, schematic view of a left work-board, a right work-board and a base of the UV sterilization device for a board-type kitchenware in accordance with an exemplary embodiment.
Figure 2:
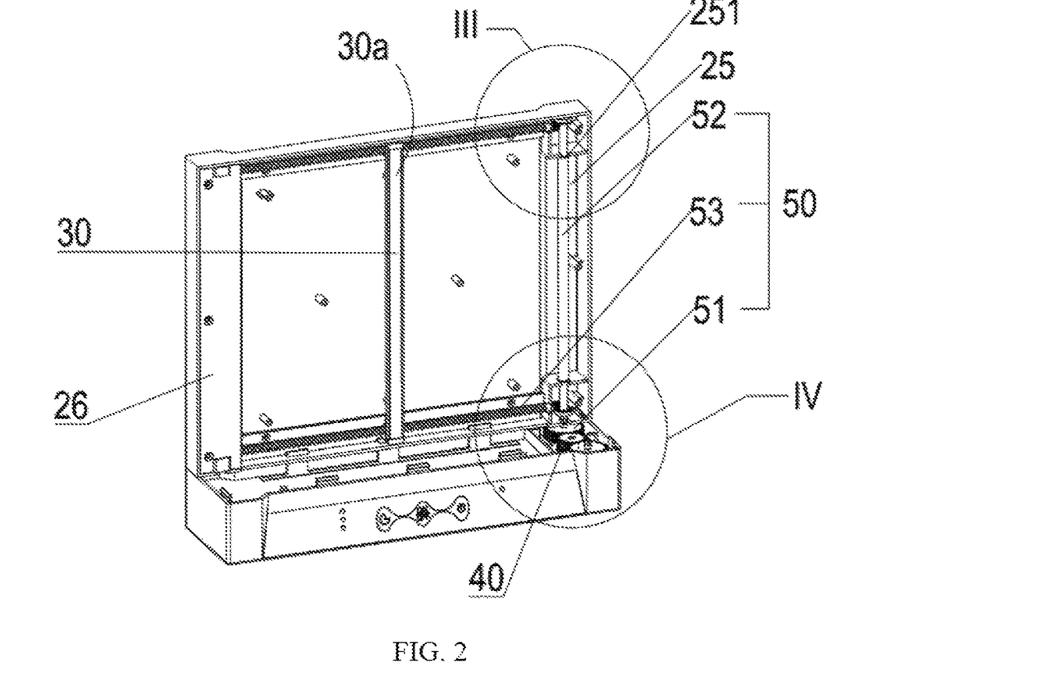
FIG. 2 is a schematic view of a transmission member of the UV sterilization device of FIG. 1.
Figure 3:
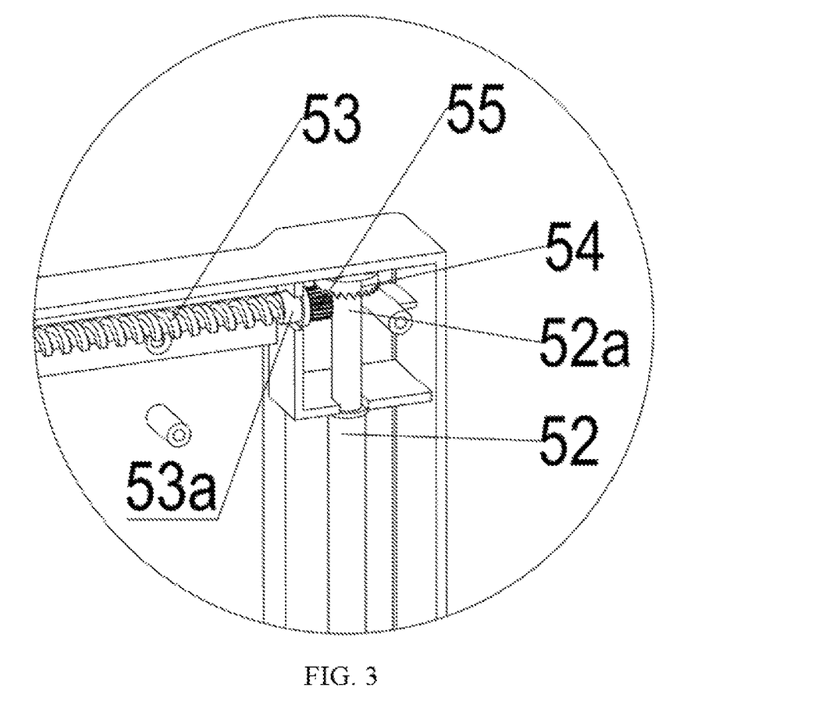
FIG. 3 is an enlarged schematic view of part III of FIG. 2.
Figure 4:
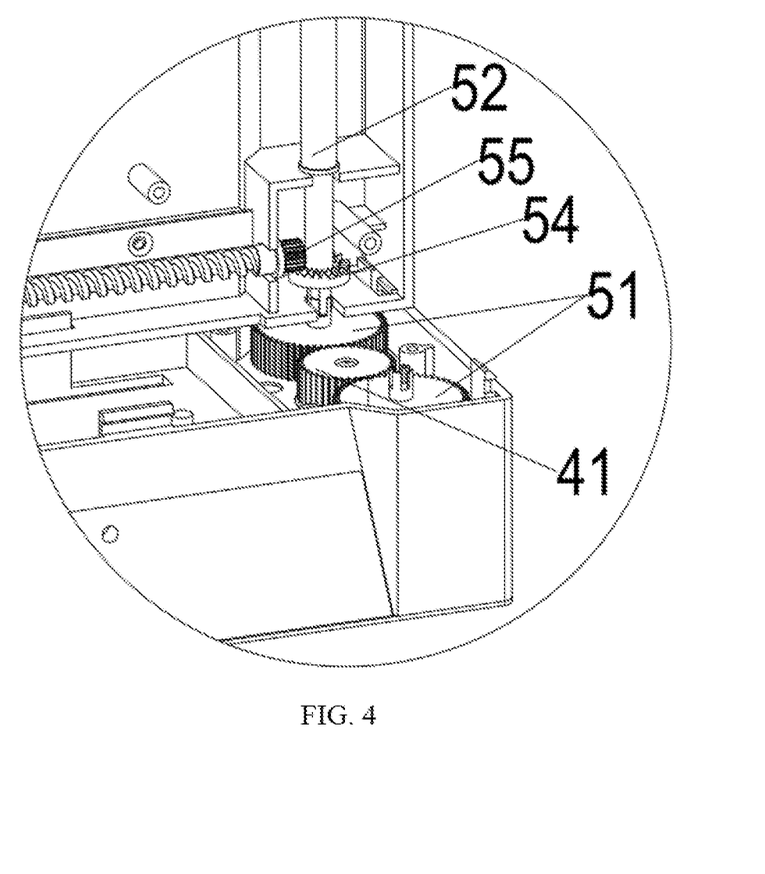
FIG. 4 is similar to FIG. 3, but shown part IV of FIG. 2.
Figure 5:
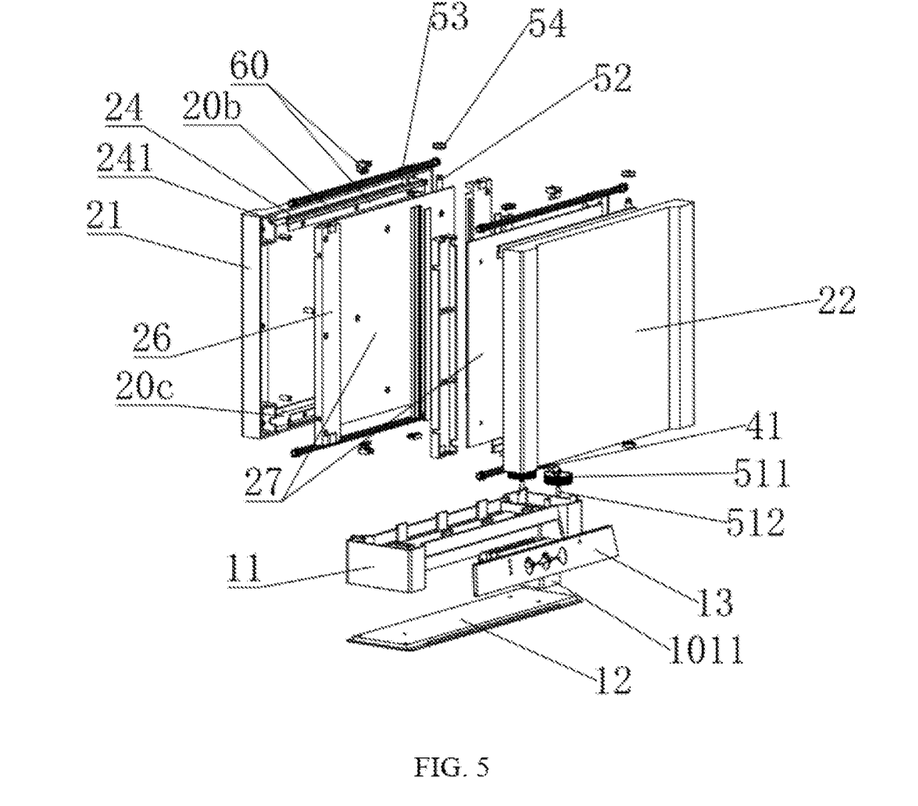
FIG. 5 is an exploded, schematic view of the UV sterilization device of FIG. 1.

Referring to FIG. 2, FIG. 4 and FIG. 5, the UV sterilization device 100 includes a rotating member 40 and a transmission member 50. The rotating member 40 includes a rotating gear 41 fixed with the first motor 1011, and the transmission member 50 includes a pair of variable gears 51 respectively arranged on both sides of the rotating gear 41 and partially meshed with the rotating gear 41, a main shaft 52 fixed with one of the pair of variable gears 51, and a pair of screw rods 53 with a corresponding end 53a thereof rotatably connected with two opposite portions 52a of the main shaft 52. Two opposite ends 30a of the UV sterilization module 30 is slidably arranged on the pair of screw rods 53, respectively. The first motor 1011 is configured to drive the rotating gear 41 to rotate and make the variable gear 51, the main shaft 52 and the pair of screw rods 53 following rotate so as to further drive the UV sterilization module 30 to slide with the pair of screw rods 53. The main shaft 52 and the variable gear 51 are detachably connected with each other, thereby fast installation and replacement by hand can be obtained.

Furthermore, the transmission member 50 further includes a pair of end cones 54 respectively fixed at the two opposite portions 52a of the main shaft 52. The pair of screw rods 53 each includes a connecting gear 55 formed on a portion adjacent to the main shaft 52, and the pair of end cones 54 is partially meshed, with a corresponding connecting gear 55 so as to rotatably connect the pair of screw rods 53 and the main shaft 52. It can be seen that the pair of end cones 54 of the present disclosure is played as a role of transition connection.

As an exemplary embodiment of the present disclosure, referring to FIG. 2 and FIG. 5, the UV sterilization device 100 further includes a sliding rail 60 to maintain the linear motion stability of the UV sterilization module 30. Each of the left work-hoard 21 and the right work-board 22 includes a lateral first receiving slot 24 formed on their respective top inner side 20b and bottom inner side 20c for receiving the sliding rail 60 therein.

Preferably, each of the left and right work-hoards 21, 22 includes a longitudinal second receiving slot 25 on their respective both sides to connect with the first receiving slot 24. All the main shaft 52 and the pair of end cones 54 are received in one of the second receiving slots 25. A front cover 26 is arranged on each of the left work-board 21 and the right work-board 22 and covered on the second receiving slot 25.

Furthermore, the first receiving slot 24 includes a first U-shaped slot 241 for fixing with the pair of screw rods 53, and the second receiving slot 25 includes a second U-shaped slot 251 for fixing with the main shaft 52.

Figure 7:
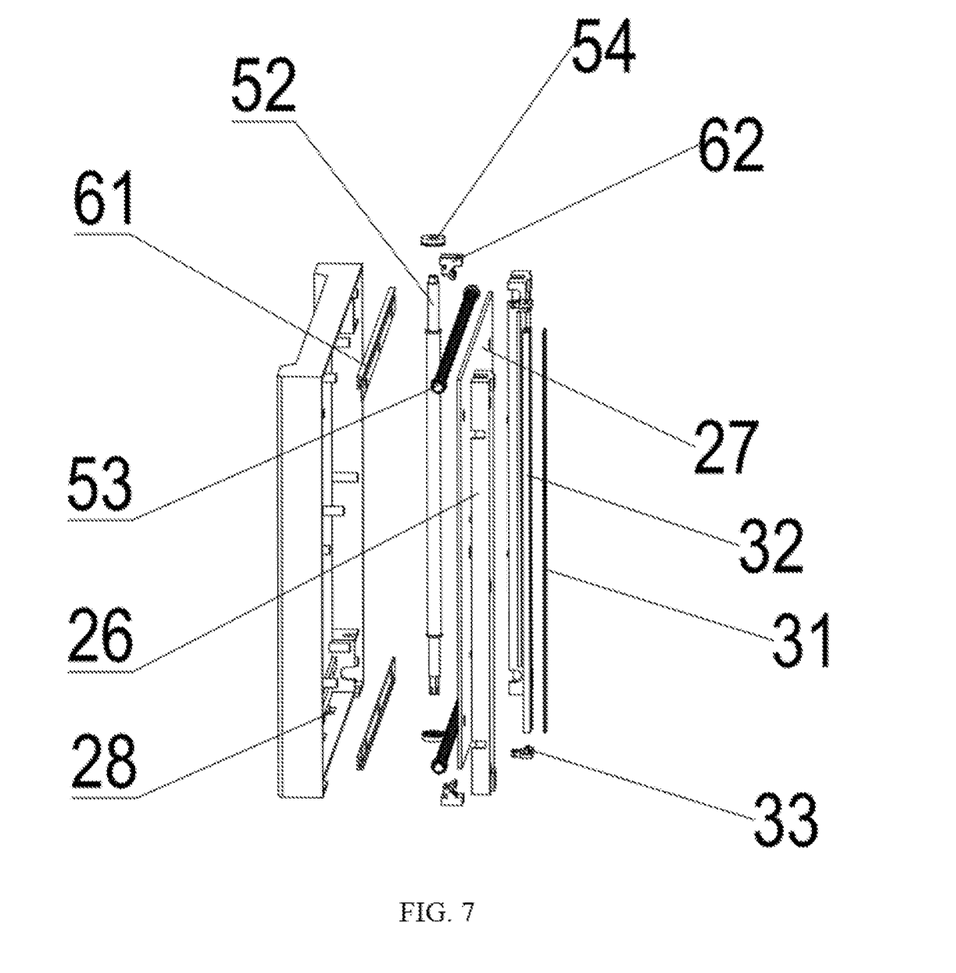
FIG. 7 is an exploded, schematic view of the left work-board or the right work-board of the UV sterilization device of FIG. 1.
Figure 9:
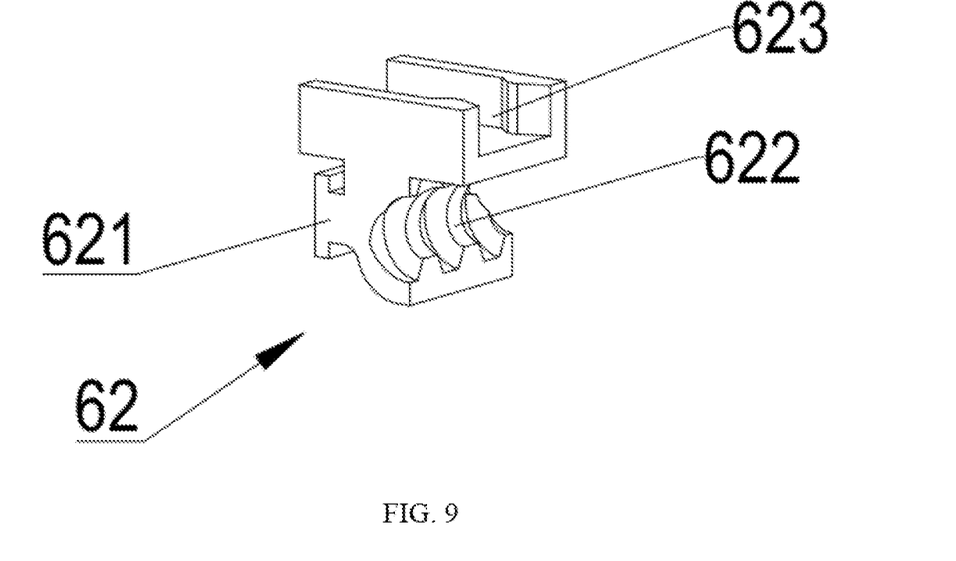
FIG. 9 is a schematic view of a sliding block of the UV sterilization device of FIG. 1.

Referring to FIG. 5, FIG. 7 and FIG. 9, the sliding rail 60 includes a sliding groove 61 and a sliding block 62 sliding relative to the sliding groove 61. The sliding block 62 includes a sliding portion 621 slidably arranged on the sliding groove 61, a thread groove 622 meshed with the screw rod 53 and a inserting slot 623 for inserting the UV sterilization module 30 therein, thereby fast tool-less installation and replacement can be obtained. Furthermore, the thread groove 622 is semicircular configuration and matched with the shape of the screw rod 53.

Because the screw rod 53 is meshed with the thread groove 622, when the main shaft 52 drives the screw rod 53 to rotate, the thread groove 622 will slide along the thread trajectory of the screw rod 53. At this time, the sliding portion 621 is followed to slide in the sliding groove 61 to further drive the UV sterilization module 30 inserted in the inserting slot 623 to parallel slide. Thus, the parallel slide of the UV sterilization module 30 is to smoothly proceed.

Preferably, the sliding groove 61 is a T-shaped configuration and the sliding portion 621 is a T-shaped plate. Thus, the UV sterilization module 30 can move left and right in a straight line along the T-shaped sliding groove 61, which can prevent the sliding portion 621 from accidentally falling out of the sliding groove 621 and improve the stability therebetween.

Furthermore, the left work-board 21 and, the right work-board 22 respectively include a reflecting plate 27 mounted between their respective front covers 26. The reflecting plate 27 is made of aluminum for reflecting UV light and increasing sterilization efficiency of the UV sterilization device 100.

Figure 8:
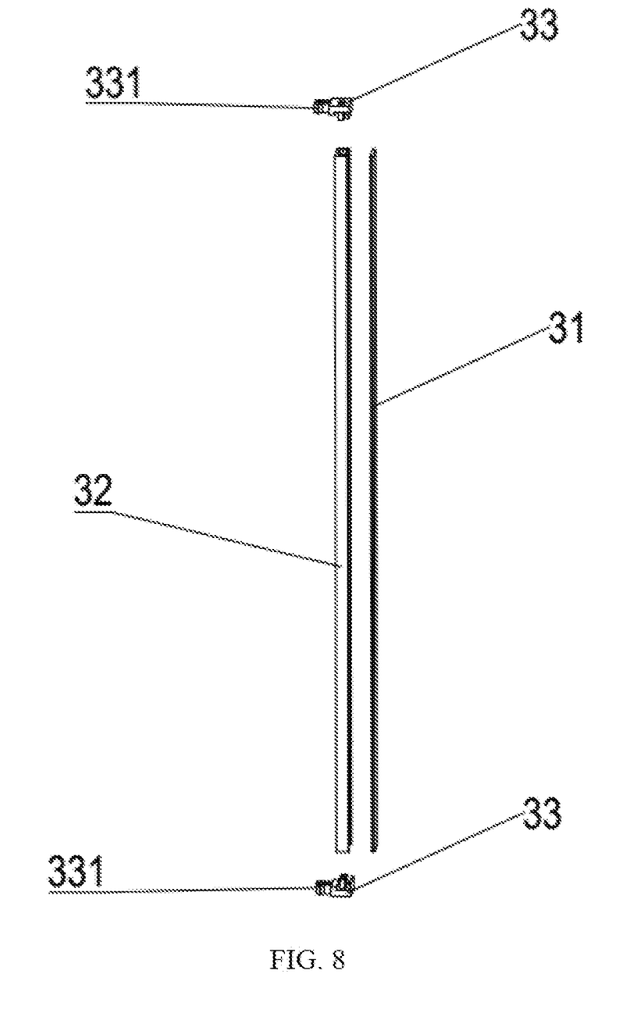
FIG. 8 is an exploded, schematic view of a UV sterilization module of the UV sterilization device of FIG. 1.

Referring to FIG. 8 and FIG. 9, the UV sterilization module 30 includes a surface plate 31, a heat dissipation shell 32 fixed with the surface plate 31, and an end cap 33 arranged on two ends of the surface plate 31 and the heat dissipation shell 32. The end cap 33 includes a buckle 331 inserted into the inserting slot 623 for connecting the UV sterilization module 30 and the sliding block 62. Furthermore, the surface plate 31 is made of a material with high UV transmission rate to enable the UV light to conveniently pass therethrough so as to further improve sterilization effect of the board-type kitchenware 200. The UV sterilization module 30 is connected with the sliding block 62 via the buckle 331, thereby fast tool-less installation and replacement can be obtained.

Figure 6:
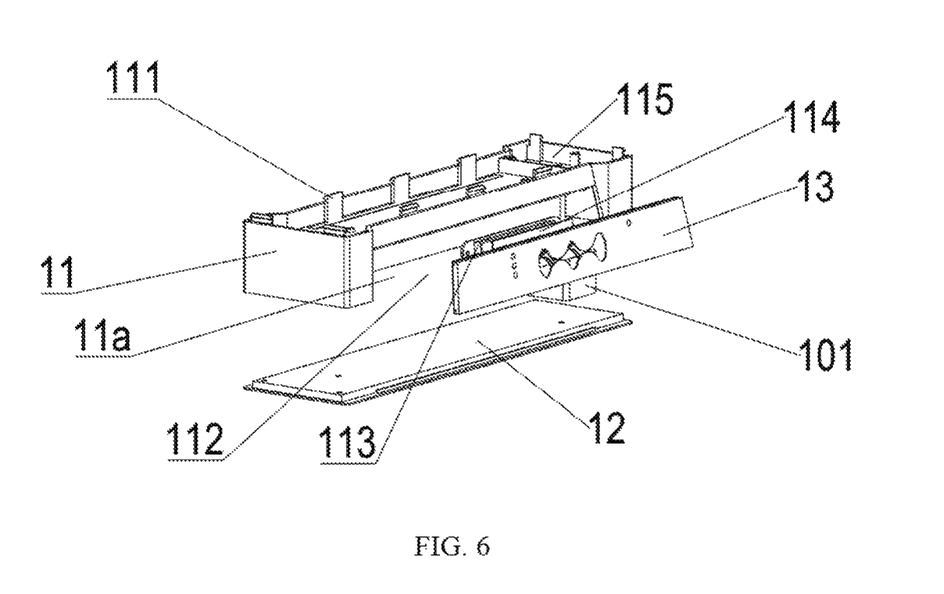
FIG. 6 is a schematic view of the base of the UV sterilization device of FIG. 1.

Referring to FIG. 6 and FIG. 7, the base 10 includes a main body 11, a base plate 12 fixed with the bottom of the main body 11 and a switching panel 13. The main body 11 includes a hooking portion 111 and an installing groove 112 formed on a lower side end 11a of the main body 11. The installing groove 112 includes a touching tablet 113 and a touching PCB 114 formed therein. Each of the left and right work-boards 21, 22 includes a snapping hole 28 engaged with the hooking portion 111 for fixing the base 10 with the left and right work-boards 21, 22. The switching panel 13 is covered on the installing groove 112. The base 10 and the left and right work-boards 21, 22 are fixed with each other by means of plug-in way, which is convenient to install and replace so as to further obtain fast installation and disassemble by hand.

Furthermore, the main body 11 includes a receiving recess 115 for receiving the rotating gear 41 therein, and the variable gear 51 includes a housing 511 and a gear shaft 512. The housing 511 is fixed into the receiving recess 115 via the gear shaft 512.

Figure 10:
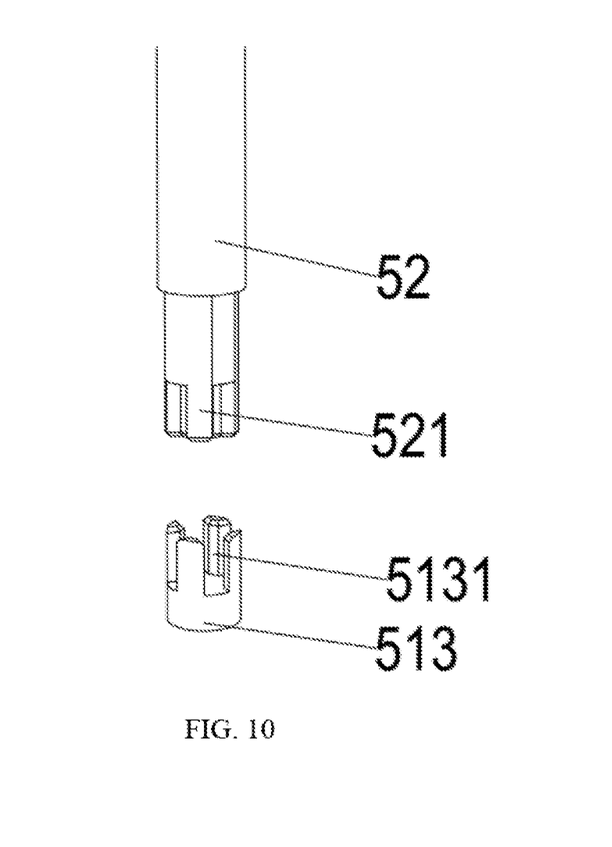
FIG. 10 is a partial exploded, schematic view of an inserting rod and a main shaft of the UV sterilization device of FIG. 1.

Referring to FIG. 10, the main shaft 52 includes a plurality of ribs 521 protruding outward from the bottom thereof, and the inserting rod 513 is connected with the upper of the gear shaft 512 and includes an opening slot 5131. The rib 521 is inserted into the opening slot 5131 for fixing the main shaft 52 with the variable gear 51. The main shaft 52 and the variable gear 51 are fixed with each other by means of plug-in way, which is convenient to fast installation and replacement.

Figure 11:
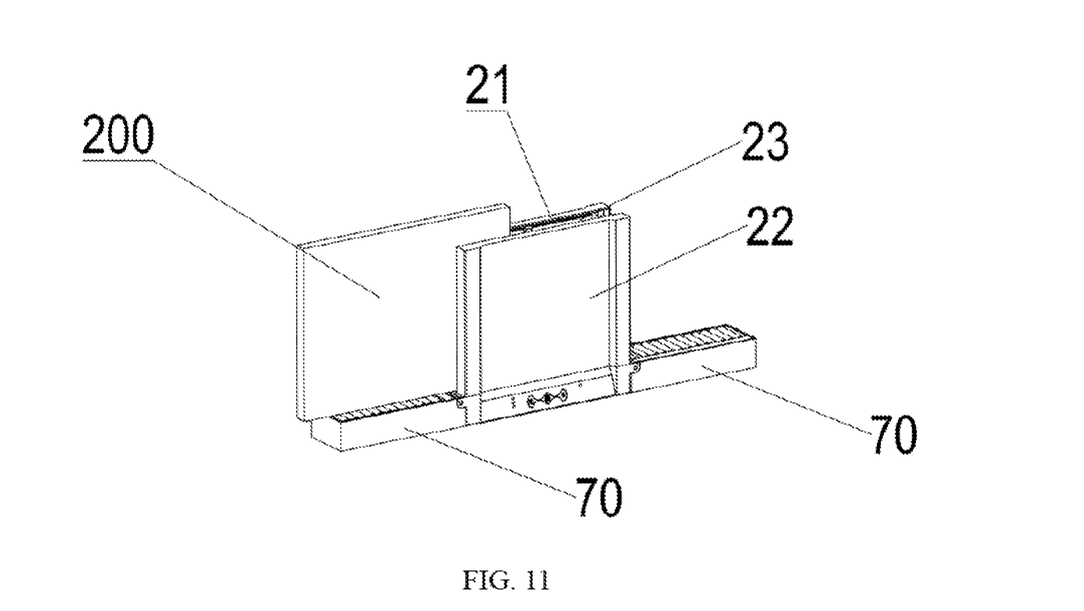
FIG. 11 is an assembly schematic view of the left work-board, the right work-board, the base and a pair of transmission boxes of the sterilization device of FIG. 1.
Figure 12:
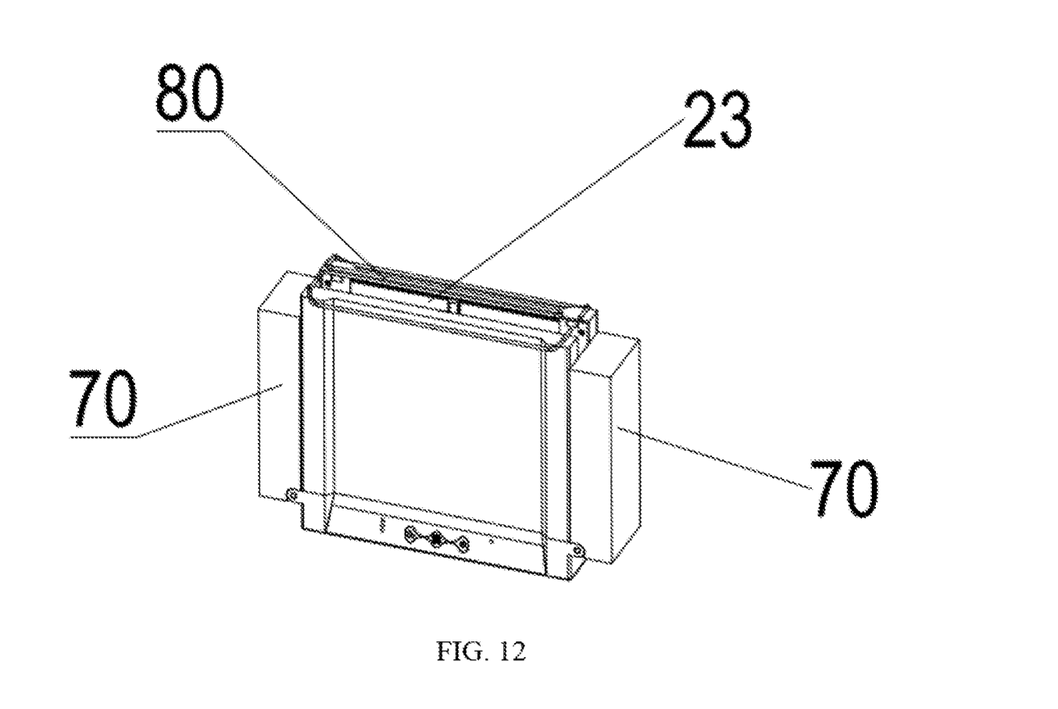
FIG. 12 is similar to FIG. 11, but shown the pair of transmission boxes in the other state.

As an exemplary embodiment of the present disclosure, referring to FIG. 11, the UV sterilization device 100 further includes a pair of transmission boxes 70 respectively arranged on two opposite sides 10a of the base 10 and axially connected with the base 10 so that the board-type kitchenware 200 positioned on the pair of transmission boxes 70 can be fed into or discharged out of the receiving room 23. The pair of transmission boxes 70 is provided that the sterilization process of the board-type kitchenware 200 is more simple and convenient so that the board-type kitchenware 200 can't be fed into or discharged out of the receiving room 23, manually.

Preferably, the transmission box 70 includes a transmitting body 71, a transmitting device 72 received in the transmitting body 71 and a power plant 73 fixed on a sidewall of the transmitting body 71. The power plant 73 is configured to drive the transmitting device 72 to rotate so that the board-type kitchenware 200 positioned on the pair of transmission boxes 70 can be fed into or discharged out of the receiving room 23.

Figure 13:
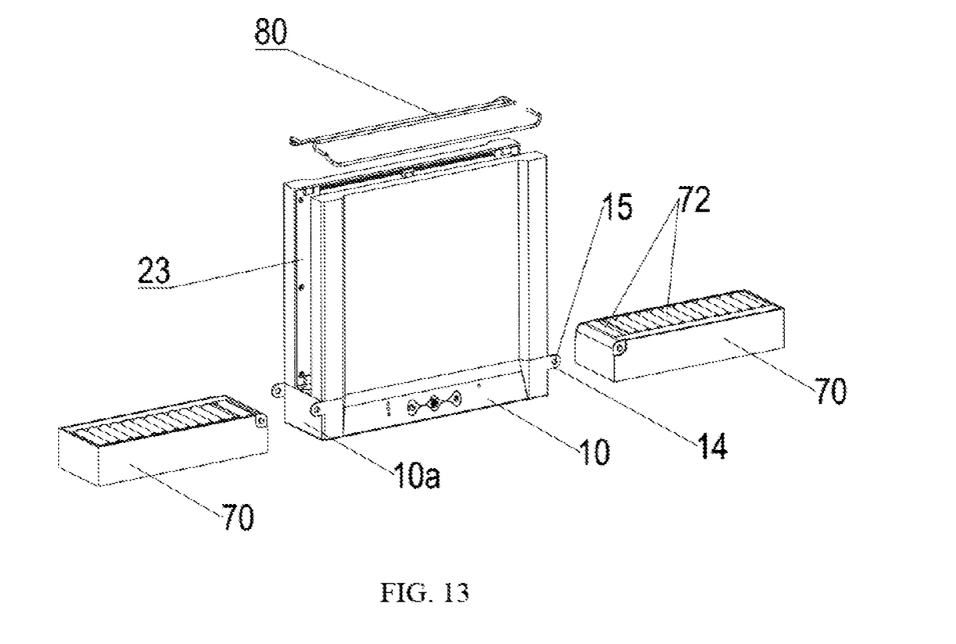
FIG. 13 is similar to FIG. 11, but shown the pair of transmission boxes and a tableware hook in a disassembled state.
Figure 14:
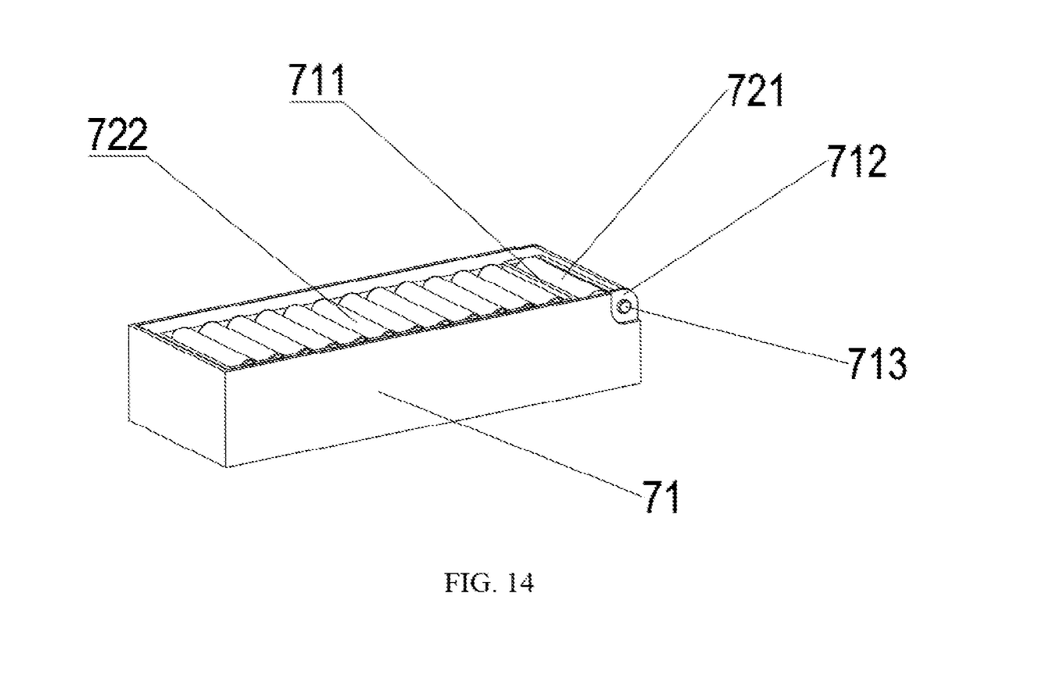
FIG. 14 is a schematic view of the transmission box of the UV sterilization device of FIG. 1.
Figure 15:
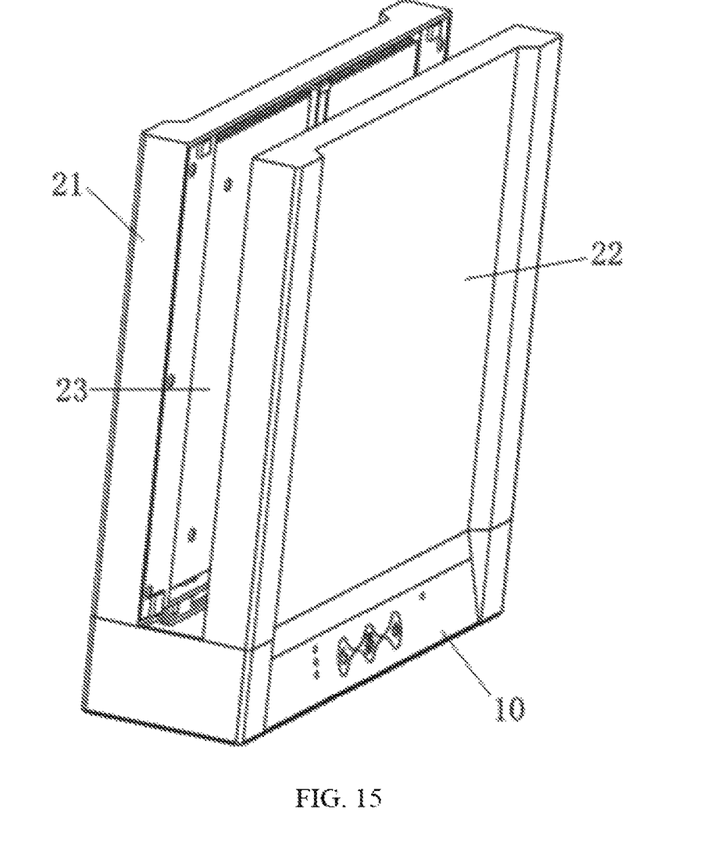
FIG. 15 is an assembly schematic view of the left work-board, the right work-board and the base of the UV sterilization device of FIG. 1.
Figure 16:
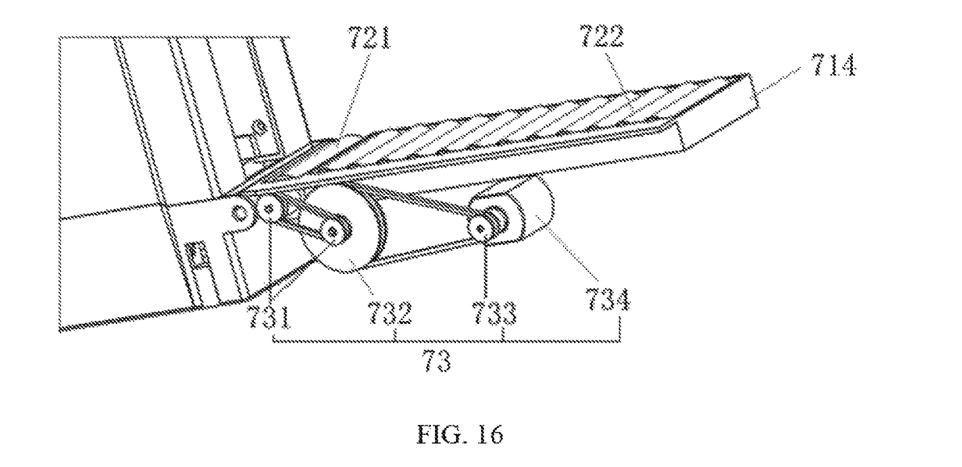
FIG. 16 is a schematic view of the transmission box of the UV sterilization device of FIG. 14, but not shown a transmitting body thereof.
Figure 17:
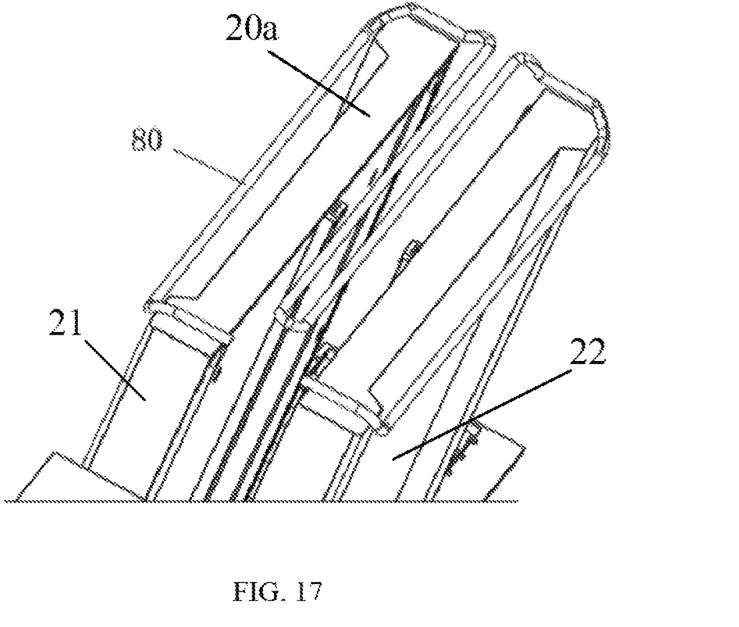
FIG. 17 is an enlarged, assembly schematic view of the tableware hook, the left work-board and the right work-board of the UV sterilization device of FIG. 13.
Figure 18:
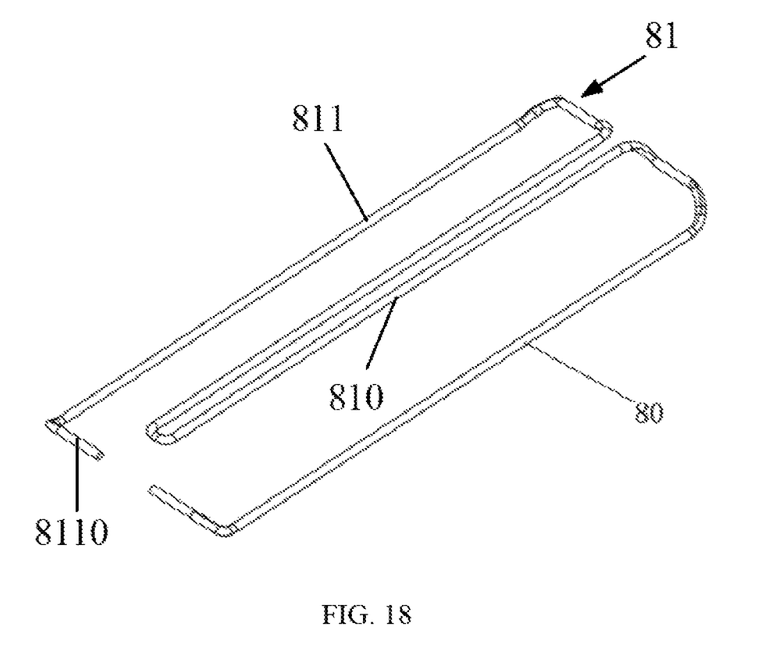
FIG. 18 is a schematic view of the tableware hook of the UV sterilization device of FIG. 13.

Furthermore, referring to FIG. 13, FIG. 14 and FIG. 16, the transmitting device 72 includes an active roller 721 and a passive roller 722, and the transmitting body 71 includes a rim 714 for accommodating the active roller 721 and the passive roller 722 thereon. The rim 714 includes a partition 711 for separating the active roller 721 from the passive roller 722. The power plant 73 includes a pair of first pulleys 731, a large-diameter pulley 732, a small-diameter pulley 733 and a second motor 734. The active roller 721 is sleeved around one of the first pulleys 731, the other first pulley 731 is coaxially fixed with the large-diameter pulley 732, and the small-diameter pulley 733 is fixedly connected with the second motor 734.

The board-type kitchenware 200 is positioned on the active roller 721 and the second motor 734 drives the active roller 721 to rotate so that the board-type kitchenware 200 can move in the receiving room 23 under the rotation of the active roller 721. When the board-type kitchenware 200 is fully received in the receiving room 23, the pair of transmission boxes 70 is rotated to cover the two opposite sides of the receiving room 23, respectively, thereby the board-type kitchenware 200 can be sterilized by the UV sterilization module 30. When the board-type kitchenware 200 is completely sterilized, the board-type kitchenware 200 is then transferred to the other transmission box 70 to further be driven to move out of the receiving room 23 until the board-type kitchenware 200 is finally clamped to be collected into cabinets by clean clamps. Meanwhile, each second motor 734 of the pair of transmission boxes 70 is rotated along two opposite directions so that the board-type kitchenware 200 can be fed into or discharged out of the receiving room 23.

Preferably, the base 10 includes a pedestal 14 protruding outward from two opposite sides 10a thereof. The pedestal 14 includes an installing hole 15, and the transmitting body 71 includes a connecting recess 712 attached to the inner wall of the pedestal 14 and an installing shaft 713 sleeved on the installing hole 15, thereby the transmission box 70 can be rotated around the pedestal 14 in a range of 0-90 degrees. The pair of transmission boxes 70 is detachably installed on the UV sterilization device 100 to further improve its convenient usage. The pair of transmission boxes 70 can rotate around the pedestal 14 to cover both sides of the receiving room 23, thereby the sterilization effect of the UV sterilization device 100 can be improved.

In an exemplary embodiment of the present disclosure, each of the left work-board 21 and the right work-board 22 includes a tableware hook 80 formed on their respective upper portions 20a thereof. The tableware hook 80 is bent by a stainless steel rod to form a shape shown in FIGS. 13, 17-18. The tableware hook 80 is bent to form two U-shaped structures 81 thereon. Each of the two U-shaped structures 81 includes a middle rod 810, a lateral rod 811 connected to the middle rod 810 and an end portion 8110 formed on a distal end of the lateral rod 811. The two middle rods 810 are close to each other and the two end portions 8110 are bent towards each other. The distance between the two middle rods 810 and the upper portion 20a of the left and right work-boards 21, 22 is greater than the distance between the two lateral rods 811 and the upper portion 20a of the left and right work-boards 21, 22. While, the distance between the two end portions 8110 and the upper portion 20a of the left and right work-boards 21, 22 is greater than the distance between the two lateral rods 811 and the upper portion 20a of the left and right work-boards 21, 22. The tableware hook 80 can be directly positioned on the upper portion 20a of the left work-board 21 and the right work-board 22 so that the middle rod 810 of the U-shaped structure 81 is arranged above the receiving room 23, and the lateral rod 811 is positioned on the upper portion 20a of the left and right work-boards 21, 22. In this way, the tableware can be hung on the middle rod 810 and then enter the receiving room 23 for disinfection. After the tableware is completely sterilized, the tableware can be easily used as long as the tableware hook 80 is removed.

In used the board-type kitchenware 200 is placed in the receiving room 23 formed between the left work-board 21 and the right work-board 22, the first motor 1011 drives the rotating gear 41 to rotate and then drives the pair of variable gears 51 to rotate forward and backward, respectively. And then, the main shaft 52 fixedly connected to the variable gear 51 is driven to follow rotating, the pair of end cones 54 can be driven to rotate along the same direction of the variable gear 51. In this way, the pair of screw rods 53 is also driven to rotate under the action of a corresponding end cone 54, the sliding block 62 is also driven to move along the screw rod 53 in the straight line and simultaneously slide in the sliding groove 61. The UV sterilization module 30 is fixedly connected with the sliding block 62 via the buckle 331, therefore, the UV sterilization module 30 can follow the sliding block 62 to move in the straight line together with the screw rod 53, thereby the horizontal reciprocating movement of the UV sterilization module 30 is obtained and the sterilization of the board-type kitchenware 200 placed in the receiving room 23 is also obtained.

Although the features and elements of the present disclosure are described as embodiments in particular combinations, each feature or element can be used alone or in other various combinations within the principles of the present disclosure to the full extent indicated by the broad general meaning of the terms in which the appended claims are expressed.

What is claimed is:

1. A UV sterilization device for a board-type kitchenware comprising:
    a base comprising a driving member received therein, and the driving member comprising a first motor;
    a work-board comprising a left work-board and a right work-board, the left work-board and the right work-board structurally consistent with each other and symmetrically connected to front and rear sides of the base respectively, and a receiving room formed between the left work-board and the right work-board for receiving the board-type kitchenware therein;
    a UV sterilization module longitudinally arranged on the inside of the left and right work-boards and horizontally sliding relative to the left and right work-boards; and wherein
    the first motor is connected with the UV sterilization module and configured to drive the UV sterilization module to slide so as to sterilize the board-type kitchenware received in the receiving room; and wherein
    the UV sterilization device further comprises a pair of transmission boxes respectively arranged on two opposite sides of the base and axially connected with the base so that the board-type kitchenware positioned on the pair of transmission boxes can be fed into or discharged out of the receiving room.

2. The UV sterilization device as claimed in claim 1, wherein the UV sterilization device further comprises a rotating member and a transmission member, the rotating member comprising a rotating gear fixed with the first motor, and the transmission member comprising a pair of variable gears respectively arranged on both sides of the rotating gear and partially meshed with the rotating gear, a main shaft fixed with one of the pair of variable gears, and a pair of screw rods with a corresponding end thereof rotatably connected with two opposite portions of the main shaft; two opposite ends of the UV sterilization module slidably arranged on the pair of screw rods, respectively, the first motor configured to drive the rotating gear to rotate and make the variable gear, the main shaft and the pair of screw rods rotate so as to further drive the UV sterilization module to slide with the pair of screw rods.

3. The UV sterilization device as claimed in claim 2, wherein the transmission member further comprises a pair of end cones respectively fixed at the two opposite portions of the main shaft, the pair of screw rods each comprising a connecting gear formed on a portion adjacent to the main shaft, the end cone partially meshed with a corresponding connecting gear so as to rotatably connect the pair of screw rods and the main shaft.

4. The UV sterilization device as claimed in claim 3, wherein the UV sterilization device further comprises a sliding rail, and each of the left and right work-boards comprises a lateral first receiving slot formed on their respective top inner side and bottom inner side for receiving the sliding rail therein.

5. The UV sterilization device as claimed in claim 4, wherein each of the left and right work-boards comprises a longitudinal second receiving slot on their respective both sides to connect with the first receiving slot, all the main shaft and the pair of end cones received in one of the second receiving slots, a front cover arranged on each of the left work-board and the right work-board and covered on the second receiving slot.

6. The UV sterilization device as claimed in claim 5, wherein the first receiving slot comprises a first U-shaped slot for fixing with the pair of screw rods, and the second receiving slot comprises a second U-shaped slot for fixing with the main shaft.

7. The UV sterilization device as claimed in claim 5, wherein the left work-board and the right work-board respectively comprise a reflecting plate mounted between the front covers.

8. The UV sterilization device as claimed in claim 4, wherein the sliding rail comprises a sliding groove and a sliding block sliding relative to the sliding groove, the sliding block comprising a sliding portion slidably arranged on the sliding groove, a thread groove meshed with the screw rod and an inserting slot for inserting the UV sterilization module therein.

9. The UV sterilization device as claimed in claim 8, wherein the sliding groove is a T-shaped configuration and the sliding portion is a T-shaped plate.

10. The UV sterilization device as claimed in claim 8, wherein the UV sterilization module comprises a surface plate, a heat dissipation shell fixed with the surface plate, and an end cap arranged on two ends of the surface plate and the heat dissipation shell and comprising a buckle inserted into the inserting slot for fixing the UV sterilization module with the sliding block.

11. The UV sterilization device as claimed in claim 2, wherein the base comprises a main body, a base plate fixed with the bottom of the main body and a switching panel, the main body comprising a hooking portion and an installing groove formed on a lower side end of the main body, with the installing groove comprising a touching tablet and a touching PCB therein; each of the left and right work-boards comprising a snapping hole engaged with the hooking portion for fixing the base with the left and right work-boards, and the switching panel covering on the installing groove.

12. The UV sterilization device as claimed in claim 11, wherein the main body comprises a receiving recess for receiving the rotating gear therein, and the variable gear comprises a housing and a gear shaft, the housing fixed into the receiving recess via the gear shaft.

13. The UV sterilization device as claimed in claim 12, wherein the main shaft comprises a plurality of ribs protruding outward from the bottom thereof, and the inserting rod is connected with the upper of the gear shaft and comprises an opening slot, the rib inserting into the opening slot for fixing the main shaft with the variable gear.

14. The UV sterilization device as claimed in claim 1, wherein the transmission box comprises a transmitting body, a transmitting device received in the transmitting body and a power plant fixed on a sidewall of the transmitting body, and the power plant is configured to drive the transmitting device to rotate so that the board-type kitchenware positioned on the pair of transmission boxes can be fed into or discharged out of the receiving room.

15. The UV sterilization device as claimed in claim 14, wherein the transmitting device comprises an active roller and a passive roller, and the transmitting body comprises a rim for accommodating the active roller and the passive roller thereon, the rim comprising a partition for separating the active roller from the passive roller.

16. The UV sterilization device as claimed in claim 15, wherein the power plant comprises a pair of first pulleys, a large-diameter pulley, a small-diameter pulley and a second motor, the active roller sleeved around one of the first pulleys, the other first pulley coaxially fixed with the large-diameter pulley, and the small-diameter pulley fixedly connected with the second motor.

17. The UV sterilization device as claimed in claim 14, wherein the base comprises a pedestal protruding outward from two opposite sides thereof, the pedestal comprising an installing hole, the transmitting body comprising a connecting recess attached to the inner wall of the pedestal and an installing shaft sleeved on the installing hole, and the transmission box can be rotated around the pedestal in a range of 0-90 degrees.

18. The UV sterilization device as claimed in claim 1, wherein each of the left work-board and the right work-board comprises a tableware hook formed on their respective upper portions thereof and bent to form two U-shaped structures thereon, each of the two U-shaped structures comprising a middle rod, a lateral rod connected to the middle rod and an end portion formed on a distal end of the lateral rod, the two middle rods close to each other and the two end portions bent towards each other.

19. The UV sterilization device as claimed in claim 18, wherein the distance between the two middle rods and the upper portion of the left and right work-boards is greater than the distance between the two lateral rods and the upper portion of the left and right work-boards; while, the distance between the two end portions and the upper portion of the left and right work-boards is greater than the distance between the two lateral rods and the upper portion of the left and right work-boards.

* * * * *